United States Patent
Autebert et al.

(10) Patent No.: US 10,357,770 B2
(45) Date of Patent: Jul. 23, 2019

(54) MICROFLUIDIC PROBE FOR MODULATING INSERTION OF LIQUID SPACERS

(71) Applicant: International Business Machines Corporation, Armonk, NY (US)

(72) Inventors: Julien Autebert, Rueschlikon (CH); Julien Cors, Rueschlikon (CH); Emmanuel Delamarche, Rueschlikon (CH); Govind Kaigala, Rueschlikon (CH); Xander Frank Van Kooten, Rueschlikon (CH)

(73) Assignee: International Business Machines Corporation, Armonk, NY (US)

( * ) Notice: Subject to any disclaimer, the term of this patent is extended or adjusted under 35 U.S.C. 154(b) by 272 days.

(21) Appl. No.: 14/879,281

(22) Filed: Oct. 9, 2015

(65) Prior Publication Data
US 2017/0100717 A1 Apr. 13, 2017

(51) Int. Cl.
*B01L 3/00* (2006.01)
*B01L 3/02* (2006.01)
*G01N 35/10* (2006.01)

(52) U.S. Cl.
CPC ... *B01L 3/502784* (2013.01); *B01L 3/502715* (2013.01); *B01L 3/0293* (2013.01);
(Continued)

(58) Field of Classification Search
CPC ......... B01L 3/502784; B01L 3/502715; B01L 2200/143; B01L 2200/027; B01L 3/0293;
(Continued)

(56) References Cited

U.S. PATENT DOCUMENTS

| 8,695,639 B2 | 4/2014 | Delamarche et al. |
| 2004/0163961 A1* | 8/2004 | Timperman ..... G01N 27/44756 204/451 |

(Continued)

FOREIGN PATENT DOCUMENTS

WO 2014132139 A2 9/2014

OTHER PUBLICATIONS

Ainla, Alar, et al., "Hydronamic Flow confinement Technology in Microfluidic Perfusion Devices", Micromachines 2012,3,442-461, 20 pgs.

(Continued)

*Primary Examiner* — Lore R Jarrett
(74) *Attorney, Agent, or Firm* — Harrington & Smith

(57) ABSTRACT

A microfluidic probe is disclosed. The microfluidic probe includes a probe head, a liquid spacer supply and a spacer modulation unit. The probe head may include a processing liquid channel in fluid communication with a processing liquid aperture provided on a face of the probe head. The probe head is configured to transport, circulate, recirculate, or move some processing liquid in (or via) the processing liquid channel toward and/or from the processing liquid aperture. The spacer supply is fluidly connected, via a spacer insertion junction, to the processing liquid channel. The spacer supply is configured for inserting liquid spacers into the processing liquid channel, via the spacer insertion junction. Liquid volumes can be obtained, which are separated by inserted liquid spacers. The spacer modulation unit is configured to control the spacer supply, to modulate the insertion of spacers via the spacer supply. Related devices and methods of operation are disclosed.

18 Claims, 7 Drawing Sheets

(52) U.S. Cl.
CPC . *B01L 2200/027* (2013.01); *B01L 2200/0673* (2013.01); *B01L 2200/143* (2013.01); *B01L 2300/021* (2013.01); *B01L 2400/0487* (2013.01); *G01N 2035/1034* (2013.01)

(58) Field of Classification Search
CPC ....... B01L 2400/0487; B01L 2300/021; B01L 2200/0673; G01N 2035/1034
See application file for complete search history.

(56) References Cited

U.S. PATENT DOCUMENTS

| | | | |
|---|---|---|---|
| 2006/0003439 A1* | 1/2006 | Ismagilov | B01F 5/0471 435/287.2 |
| 2007/0039866 A1* | 2/2007 | Schroeder | G01N 27/44769 210/265 |
| 2010/0176089 A1 | 7/2010 | Delamarche et al. | |
| 2012/0048391 A1* | 3/2012 | Delamarche | B01J 19/0046 137/15.01 |
| 2014/0090715 A1 | 4/2014 | Delamarche et al. | |

OTHER PUBLICATIONS

Gervais, T., et al., "Systematic analysis of microfluidic probe design and operation", Engineering in Medicine and Biology Scoeity (EMBC), 2014 36th Annual International Conference of the IEEE, abstract only.

Juncker, David, et. al., "Multipurpose microfluidic probe", Nature Materials 4, 622-628 (2005), Published online: Jul. 24, 2005, abstract only.

Autebert, J., et al., "Nested Hydrodynamic Flow Confinement and Liquid Recirculation: Microscale Probing and Patterning of Biological Surfaces", 18th International Conference of Miniaturized Systems for Chemistry and Life Sciences, Oct. 26-30, 2014, San Antonio, Texas, USA, 3 pgs.

* cited by examiner

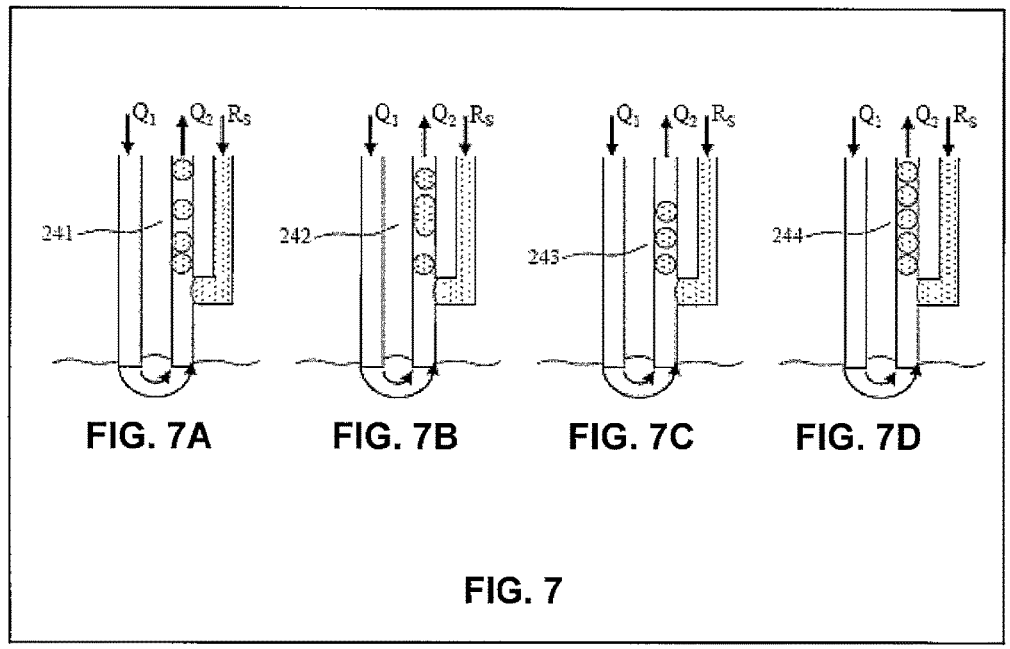
FIG. 7A   FIG. 7B   FIG. 7C   FIG. 7D
FIG. 7
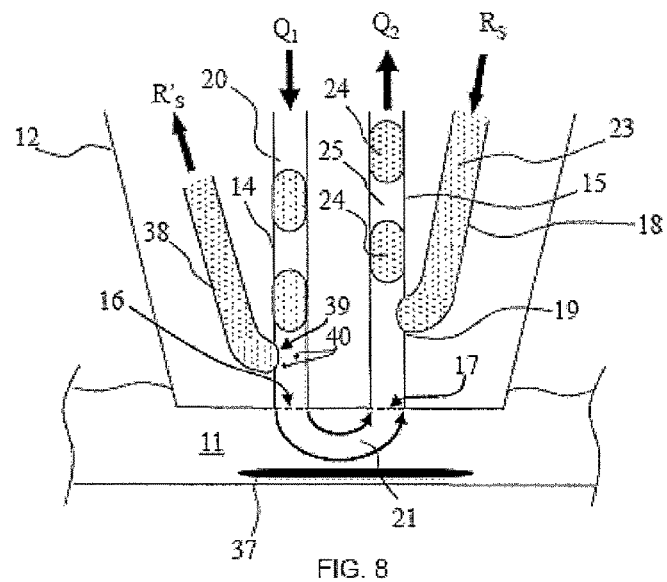
FIG. 8

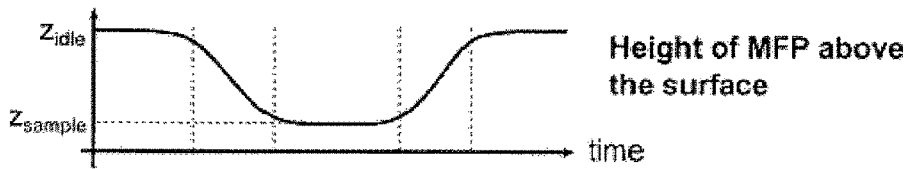
FIG. 11A
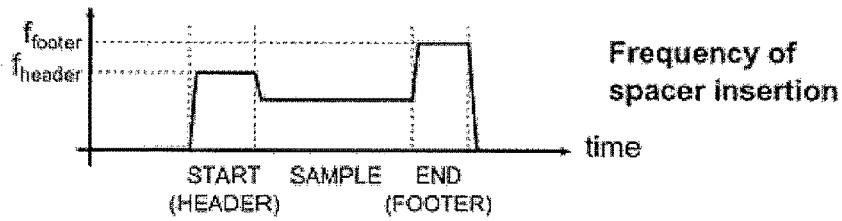
FIG. 11B
FIG. 11
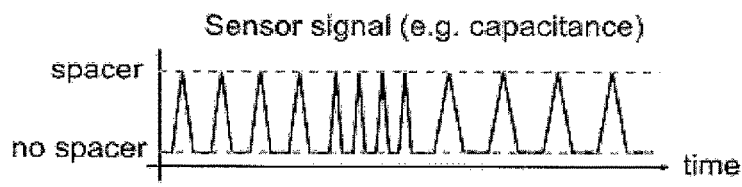
FIG. 12A
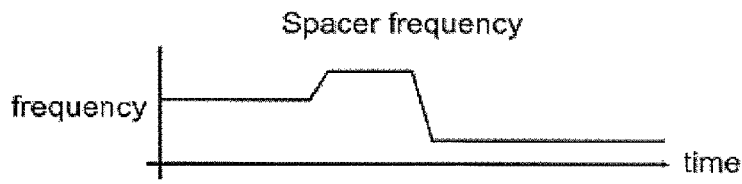
FIG. 12B
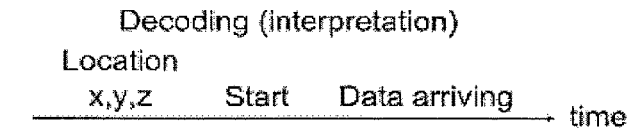
FIG. 12C
FIG. 12

MICROFLUIDIC PROBE FOR MODULATING INSERTION OF LIQUID SPACERS

FIELD

The invention relates in general to the field of microfluidic probe probes and, in particular, to microfluidic probes enabling insertion of liquid spacers, e.g., separating liquid volumes as well as, e.g., methods for inserting liquid spacers to separate liquid volumes transported in such probes.

BACKGROUND

Microfluidics deals with the behavior, precise control and manipulation of small volumes of fluids that are typically constrained to micrometer-length scale channels and to volumes typically in the sub-milliliter range. Prominent features of microfluidics originate from the peculiar behavior that liquids exhibit at the micrometer length scale. Flow of liquids in microfluidics is typically laminar. Volumes well below one nanoliter can be reached by fabricating structures with lateral dimensions in the micrometer range. Reactions that are limited at large scales (by diffusion of reactants) can be accelerated. Finally, parallel streams of liquids can possibly be accurately and reproducibility controlled, allowing for chemical reactions and gradients to be made at liquid/liquid and liquid/solid interfaces More in detail, typical volumes of fluids in microfluidics range from $10^{-15}$ L to $10^{-5}$ L and are transported, circulated or more generally moved via microchannels with a typical diameter of $10^{-7}$ in to $10^{-4}$ m. At the microscale, the behavior of fluids can differ from that at a larger, e.g., macroscopic, scale, such that surface tension, viscous energy dissipation and fluidic resistance may become dominant characteristics of the fluid flow. For instance, in microfluidics, the Reynolds number, which compares the effects of fluid momentum and viscosity, may decrease to such an extent that the flow behavior becomes laminar rather than turbulent.

In addition, at the microscale, fluids do not necessarily chaotically mix as at the microscale due to absence of turbulence in low Reynolds number flows, and interfacial transport of molecules or small particles between adjacent fluids often takes place through diffusion. As a consequence, certain chemical and physical fluid properties (such as concentration, pH, temperature and shear force) may become deterministic. This makes it possible to obtain more uniform chemical reaction conditions and higher grade products in single and multi-step reactions.

Microfluidic devices generally refer to microfabricated devices, which are used for pumping, sampling, mixing, analyzing and dosing liquids. A microfluidic probe is a device for depositing, retrieving, transporting, delivering, and/or removing liquids, in particular liquids containing chemical and/or biochemical substances. For example, microfluidic probes can be used in the fields of diagnostic medicine, pathology, pharmacology and various branches of analytical chemistry. Microfluidic probes can also be used for performing molecular biology procedures for enzymatic analysis, deoxyribonucleic acid (DNA) analysis and proteomics.

Retrieving substances from surfaces is important for numerous applications, e.g., in diagnostics, pharmaceutical and life science. When substances need to be recovered from different areas, this likely causes analytes to diffuse away from their initial recovery volume, which in turn causes cross-contaminations between sequentially recovered segments of liquid.

SUMMARY

This section is meant to describe one or more exemplary embodiments and is not meant to be limiting.

According to a first aspect, the present invention is embodied as a microfluidic probe for modulating liquid spacers separating liquid volumes. The microfluidic probe may comprise: a probe head, a liquid spacer supply and a spacer modulation unit.

The probe head comprises: a processing liquid channel that is in fluid communication with a processing liquid aperture provided on a face of the probe head. The probe head is configured to transport, circulate (or recirculate) or, more generally to move some processing liquid in (or via) the processing liquid channel toward and/or from the processing liquid aperture.

The spacer supply is fluidly connected, via a spacer insertion junction, to the processing liquid channel. The spacer supply is otherwise configured for inserting liquid spacers into the processing liquid channel, via the spacer insertion junction. This way, liquid volumes can be obtained, which are separated by inserted liquid spacers.

Finally, the spacer modulation unit may be configured to control the spacer supply, so as to be able to modulate the insertion of spacers via the spacer supply.

In other embodiments, this modulation concerns a frequency (or rate) of insertion of the spacers. In variants, the modulation may concern a length of the inserted spacers or a number of spacers successively inserted in sequence.

According to another aspect, the invention is embodied as a method for modulating liquid spacers separating liquid volumes in a microfluidic probe such as described above. While moving processing liquid in the processing liquid channel toward and/or from the processing liquid aperture, liquid spacers are inserted into the processing liquid channel, via the spacer insertion junction, to obtain a sequence of liquid volumes separated by the spacers. Meanwhile, the insertion of liquid spacers is modulated. The insertion of spacers is preferably modulated so as to encode information, e.g., as to liquid volumes preceding or succeeding the modulated spacers. The encoded information can be later on appropriately decoded, e.g., while performing subsequent analyses of the liquid volumes.

Devices, apparatuses, methods embodying the present invention will now be described; by way of non-limiting examples, and in reference to the accompanying drawings.

BRIEF DESCRIPTION OF SEVERAL VIEWS OF THE DRAWINGS

FIGS. 4A-4H, illustrates a possible operation of a microfluidic probe head such as depicted in FIG. 2, according to embodiments, where FIGS. 4A-4H illustrate preferred operation steps of a microfluidic probe head such as depicted in FIG. 2, where in FIG. 4A, injection liquid is delivered via the first channel and discharges through the first aperture 16 into immersion liquid, in FIG. 4B, the target substance is detached from the target area by the laminar flow C and gets aspirated into a channel, in FIG. 4C, the target substance has now penetrated into channel and moves upwards along the channel, in FIG. 4D, the constriction is now cut off from the remaining part of the spacer fluid and forms a well-defined droplet-shaped spacer, and where the process is repeated as shown throughout FIGS. 4E-4H, except that, from this moment on, a single spacer is inserted between each liquid volume of interest;

FIG. 7, which includes FIGS. 7A-7D, illustrates various ways of modulating a liquid spacer insertion in a probe head such as depicted in FIG. 2 or 4, according to embodiments, where FIG. 7A illustrates that a spacer modulation unit may, in embodiments, be configured in the microfluidic probe so as to modulate a frequency (or rate) of insertion of the spacers, FIG. 7B illustrates that the spacer modulation unit may be configured so as to modulate the length of inserted spacers, and FIG. 7C (where three spacers are successively inserted) and 7D (where five spacers are inserted) illustrate that one may modulate the number of spacers successively inserted;

FIG. 8 is a cross-sectional, partial view of a simplified representation of a microfluidic probe head allowing for both inserting and extracting liquid spacers in distinct channels, as involved in embodiments;

FIG. 11, including FIGS. 11A and 11B, shows graphs schematically illustrating the encoding of a header and a footer (i.e., interpretable as metadata) flanking a given processing liquid volume, as involved in embodiments, where FIG. 11A is for height of MFP above the surface and FIG. 11B is for frequency of spacer insertion; and FIG. 12, including FIGS. 12A, 12B, and 12C, shows graphs schematically illustrating how information encoded in modulated spacers can be decoded, as involved in embodiments, where FIG. 12A is for a sensor signal (e.g., capacitance), FIG. 12B is for spacer frequency, and FIG. 12C is for decoding (interpretation).

Similar or functionally similar elements in the figures have been allocated the same numeral references, unless otherwise indicated. Technical features depicted in the drawings are not necessarily to scale.

DETAILED DESCRIPTION OF EMBODIMENTS OF THE INVENTION

Figure 1:
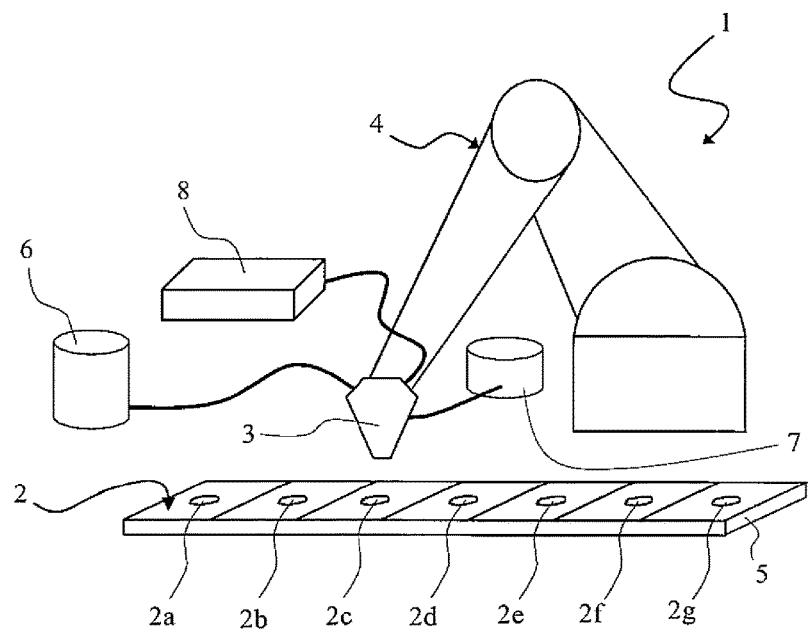
FIG. 1 shows a perspective view of a simplified representation of a microfluidic probe, according to embodiments.

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

In the following, a "fluid" refers to a "liquid" and either term may be used interchangeably.

Referring generally to FIGS. 1-12, an aspect of the invention is first described, which concerns microfluidic probes 1 for modulating liquid spacers 24. The microfluidic probe 1 basically comprises: a probe head 3, a liquid spacer supply 7 and a spacer modulation unit 31, as illustrated in, e.g., FIG. 3.

The probe head 3 first comprises a processing liquid channel 15, which is in fluid communication with a processing liquid aperture 17 provided on a face 13 of the probe head 3. The probe head 3 is generally configured to transport, (re-)circulate, or, more generally, to move processing liquid in (or via) the processing liquid channel 15 toward and/or from the processing liquid aperture 17. I.e., this probe head may be positioned with said face 13 vis-à-vis a surface to be processed thanks to the processing liquid. The head is configured to aspirate/deliver processing liquid via the processing liquid channel 15 and through the processing liquid aperture 17, from/to this surface.

The spacer supply 7 is fluidly connected to (i.e., in fluid communication with) the processing liquid channel 15, via a spacer insertion junction 19. The spacer supply 7 is generally configured for inserting liquid spacers 24 into the processing liquid channel 15, via the spacer insertion junction 19. As a result, liquid volumes 25 can be obtained, which are separated by the inserted liquid spacers 24.

Figure 2:
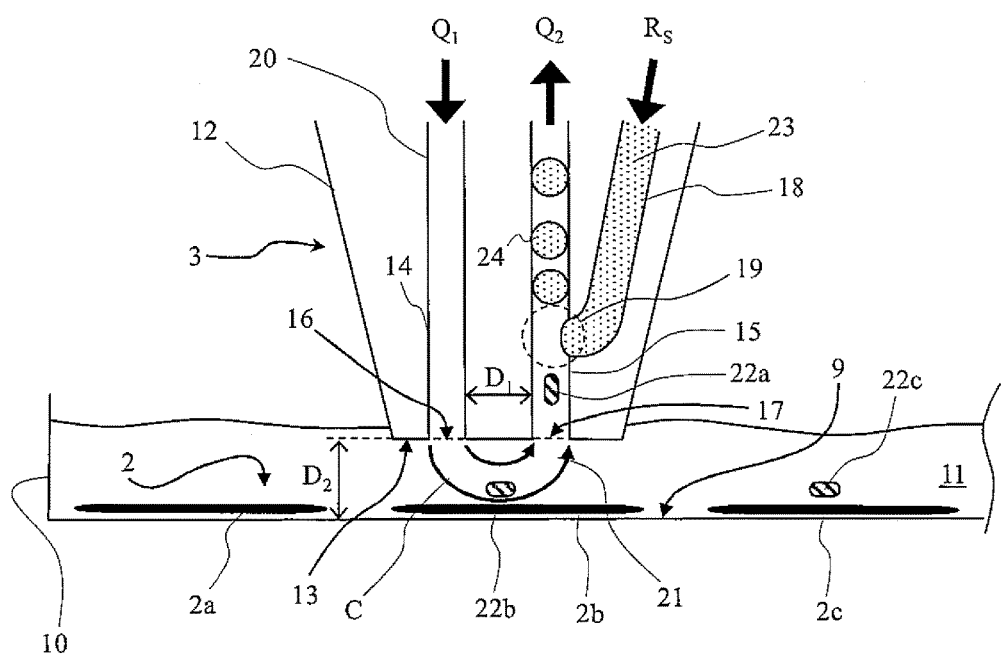
FIG. 2 is a cross-sectional, partial view of a simplified representation of a microfluidic probe head allowing for modulating liquid spacer insertion, as involved in probes according to embodiments.

The spacer modulation unit 31 comprises a t-junction of microchannels (e.g., similar to those at junction 19 of FIG. 2). The liquid spacer supply 7 is connected to the spacer modulation unit 31, and the flow results in the creation of different spacers at unit 31. The liquid spacer supply 7 is electronically controlled based on the feedback signal from the detection unit 29 that may include contact pads (and which instead may be part of spacer modulation unit 31). The contact pads may be driven by a control unit that ensures synchronization of the removal/insertion of oil spacers. Thus, the modulation of insertion of spacers is performed is a timely manner, when needed.

Modulating the insertion of spacers means physically modulating the spacers being inserted into the processing liquid channel 15. A frequency (or rate) modulation is preferably relied upon, for reasons that will become apparent later. However, other types of modulation can be contemplated. For example, one may modulate the lengths of each of the inserted spacers. In variants, one may also modulate the numbers of spacers successively inserted. Although additional chemical alteration of the spacers (e.g., Laser bleaching) can be contemplated, the primary modulation mechanisms contemplated herein involves modulation of a physical property of the inserted spacers.

As a result of modulating the spacers, different spacers or different sequences of spacers can be inserted, a thing that notably allows to encode information, e.g., addresses of processing liquid volumes (or liquid segments), or sequences of such liquid volumes. The modulated spacers can thus serve as metadata, e.g., for the (sequences of) liquid volumes they precede or follow, as discussed later in detail.

For instance, knowing the correlation between a plug and its point of origin on the processed surface 2a-2g is advantageous for conveying and maintaining spatial information related to the processed surface or samples. Rather than keeping track of the order of retrieved samples inside the channel, the present methods and devices allow the insertion of spacers to be modulated so as to encode information into the liquid flow.

In addition, single liquid spacers (i.e., not modulated) may be inserted in the processing liquid channel, in order to merely separate two processing liquid volumes. In other words, while the spacers (or sequences thereof) may be timely or occasionally modulated, the spacers may necessarily need to be constantly modulated. Single spacers may occasionally be inserted, in order to merely separate two liquid volumes.

Figure 3:
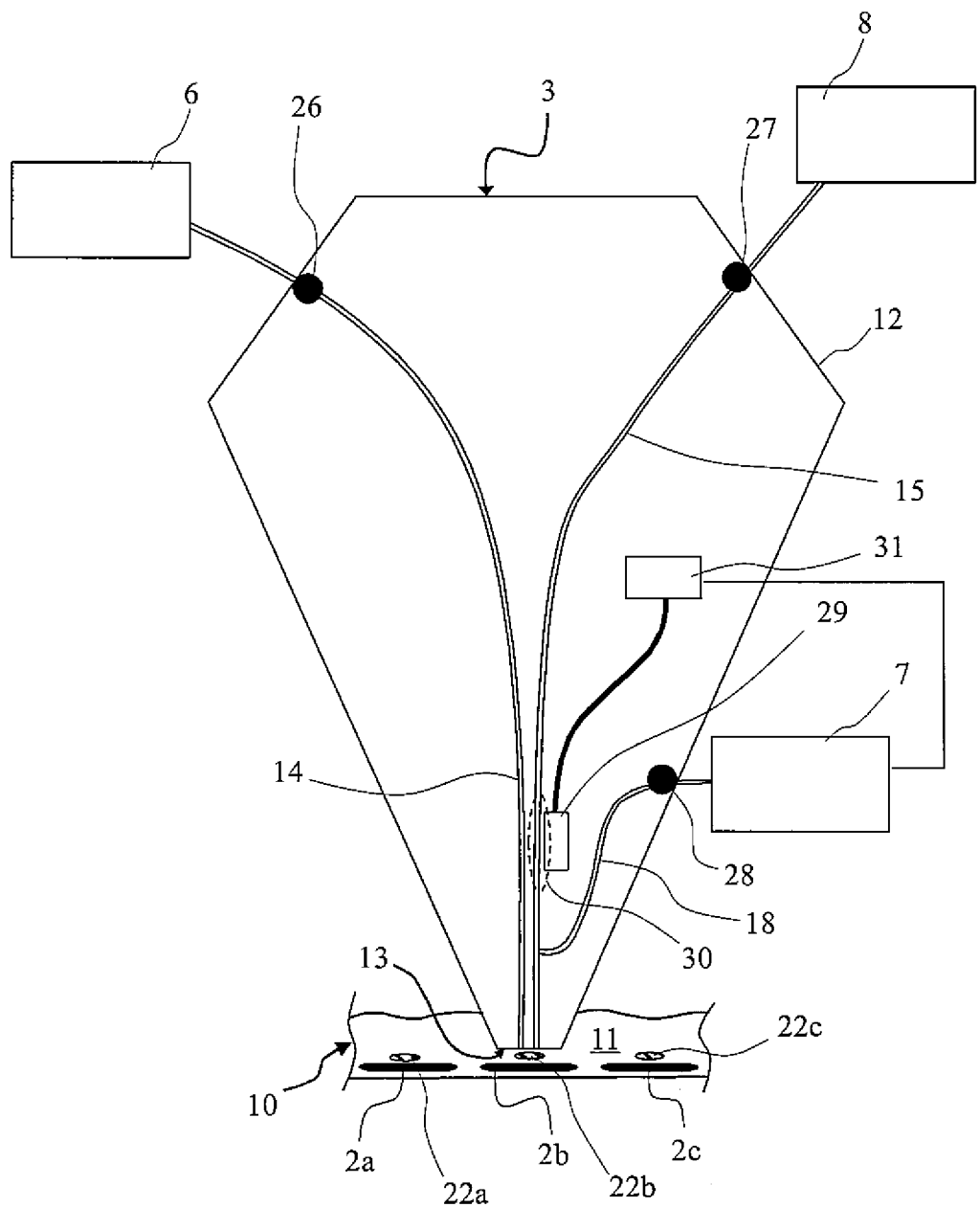
FIG. 3 shows a more comprehensive view of a probe head as in FIG. 1, notably depicting fluid connections thereto.

As illustrated in FIG. 3, the spacer modulation unit 31 can for instance be connected to a detection unit 29. The latter may be installed inside the body 12 of the probe head 3. The detection unit 29 is adapted for sensing a volume 30 inside the microchannel 15. In variants, the spacer modulation unit 31 may be part of, or contain the detection unit 29.

The detection unit 29 may be arranged upstream or downstream the spacer insertion junction 19. Two detection units may be used in variants, respectively positioned upstream and downstream the junction 19. This may be useful if the direction of circulation of the liquid flow in the channel 15 needs to be switched (i.e., reversed), notably where liquid re-circulation is contemplated, as discussed below in more details. Providing a detection unit is also useful to enable or improve the synchronization of the spacer insertion. However, the detection unit 29 is optional, inasmuch as the spacer insertion may be synchronized based on position data or other timing inputs received from other units. Suitable contact pads and electrical circuit means may be provided on the head, to that aim.

The spacer modulation unit 31 may furthermore be able to encode information, by modulating the spacer insertion, whereby the modulation is performed according to specific information to be encoded.

As evoked above, the spacer modulation unit 31 may, in embodiments, be configured in the microfluidic probe 1 so as to modulate a frequency (or rate) 241 of insertion of the spacers 24, as illustrated in FIG. 7A. That is, the modulation unit can be designed to control the frequency of spacer insertion, via the spacer supply 7. Modulating the insertion frequency results in liquid spacers being more or less spaced from each other, a thing that allows encoding of information without necessarily varying the size or the numbers of successively inserted spacers. Frequency modulation is particularly convenient as it allows for a simple operation and control of the spacer supply unit 7. For instance, frequency modulation may only require varying a pressure applied to the supply unit 7, or varying a time during which a higher pressure is applied to the supply unit 7.

In variants, the spacer modulation unit 31 may be configured so as to modulate the length 242 of inserted spacers 24, as illustrated in FIG. 7B. In other variants, one may modulate the number 243, 244 of spacers 24 successively inserted, as illustrated in FIG. 7C (where three spacers are successively inserted) and 7D (where five spacers are inserted). In all cases, a physical property of the spacers is modulated. Namely, this modulation impacts a property (such as the inter-spacer distance, the length [e.g., size] or the number) of inserted spacers (or a sequence of inserted spacers), with respect to previously inserted spacers (or a previously inserted sequence of spacers).

For completeness, the above types of modulation (frequency, length and numbers) may be combined, to allow more complex information encoding. For example, both the frequency and numbers of spacers inserted successively in a same sequence may be modulated by varying both the pressure applied to the spacer supply unit 7 and the time interval during which the pressure in varied.

Still, modulating only the frequency 241 of insertion of spacers 24 is probably the simplest modulation, as the inventors realized, as it only requires to, e.g., vary the time during which an overpressure is applied to the spacer supply unit 7.

Referring now more particularly to FIG. 1, the invention may be embodied as a microfluidic probe system that comprises a positioning system 4. The positioning system is configured for positioning the probe head 3 at given positions above a surface 2 to be processed. In addition, the positioning system may transmit position data for said given positions. In turn, the spacer modulation unit 31 may be appropriately connected to the positioning system 4 so as to be able to modulate an insertion of spacers 24 according to position data transmitted by the positioning system. The positioning system 4 may be a number of different robotics arms that comprise primarily a combination of linear stages that are available from multiple vendors (off-the-shelf), for example: from Zaber Technologies, Newport, Thorlabs, and the like.

For completeness, FIG. 1 shows a perspective view of a microfluidic probe 1 for sequentially retrieving target substances from respective target areas 2a-2g. The microfluidic probe head 3 is connected to a positioning device, in particular to a robotic arm 4. Additionally, the probe head 3 and/or the robotic arm 4 may be arranged onto a movable stage. The robotic arm 4 is configured for positioning the microfluidic probe head 3 at a specific location and, in particular, above each of the target areas 2a-2g that may typically be arranged in an array 5. Preferably, the probe 1 further comprises an x, y and z positioning stage to enable arbitrary three-dimensional movement.

In the embodiment of FIG. 1, an injection liquid supply 6, a spacer supply 7 and an analyzer 8 are, each, in fluid communication with the probe head 3. The injection liquid supply 6 supplies the probe head 3 with injection liquid 20. The spacer supply 7 provides spacer fluid 23. The retrieved target substances are delivered from the probe head 3 to the analyzer 8. Pressure sources (not shown) may further be provided, to enable insertion and/or aspiration of liquid from the supply units 6, 7, as known per se.

As illustrated in FIGS. 2-4 and 6-10, present microfluidic probes will likely include two or more processing liquid channels. Notably, the probe head 3 may comprise a first channel 14 in fluid communication with a first aperture 16 on the end face 13, e.g., for ejecting liquid toward the surface 2. The head may further comprise a second channel 15 and a second aperture 17, e.g., to aspirate liquid. Namely, the first aperture 16 and the second aperture 17 may be dimensioned and positioned at a distance so as to make it possible for the probe to aspirate at the second aperture 17 processing liquid 20 delivered through the first aperture 16. I.e., assuming given diameters for the apertures, an appropriate distance between the apertures may be imposed so as to make it possible for the probe to aspirate at the second aperture 17 processing liquid 20 delivered through the first aperture 16.

To that aim, the probe 1 may rely on hydrodynamic flow confinement (HFC) of the processing liquid. Generally speaking, HFC relates to a laminar flow of liquid, which is spatially confined within an environmental liquid (or immersion liquid) 11. Embodiments of the invention may advantageously rely on HFC, as discussed in detail below. For the sake of illustration, a hydrodynamic flow confinement of the processing liquid is mostly assumed in the following.

For instance, in the exemplary embodiment of FIG. 2, an injection microchannel 14 injects injection liquid 20 (i.e., the processing liquid) into a liquid bath with a given injection flow rate and the microchannel 15 aspirates part of the previously injected liquid and some of the background liquid with a given aspiration flow rate. By keeping the aspiration flow rate higher than the injection rate, e.g., at a defined ratio, a laminar flow path of processing liquid can be formed and confined within the immersion liquid 11.

In the embodiment of FIG. 2, the target areas 2a-2c are located on top of a bottom surface 9 of a Petri dish 10. The latter is at least partly filled with immersion liquid 11, so that the target areas 2a-2c are immersed in the immersion liquid 11.

The microfluidic probe head 3 comprises a body 12 having an end face 13. The first 14 and second 15 liquid channels are, each, formed in the body 12. Channels 14, 15 are preferably formed at an interface of two layers (e.g., by grooving a silicon substrate and closing it with a lid), according to a concept referred to as "vertical microfluidic probe head" in the literature, which simplifies the fabrication of the heads. The first 16 and second 17 apertures are, each, defined on the end face 13 of the body 12 and fluidly connected to the first and second liquid channels 14, 15, respectively. For example, a minimal distance $D_1$ between the first and second apertures may be between 0.5 μm and 10 mm, and preferably between 1.0 μm and 2.0 mm. A spacer channel 18 is fluidly connected to the second liquid channel 15 via the spacer junction 19.

The body 12 of the microfluidic probe head 3 acts as a housing or carrier. All elements, parts and/or devices integrated in the body 12 may be manufactured on-chip (using standard lithography processes, for example) and are movable therewith.

In FIG. 2, the microfluidic probe head 3 is positioned above the target area 2b. The end face 13 of the microfluidic probe head 3 is placed at a distance $D_2$ above the target area 2b, so as for the end face 13 to be immersed in the immersion liquid 11 that covers the target areas 2a-2c. For example, the distance $D_2$ may be 1-100 μm, and preferably 2-80 μm.

The injection liquid 20 is delivered via the first liquid channel 14 to the first aperture 16 with a first flow rate $Q_1$. An underpressure is applied to the second liquid channel 15 such that some of the immersion liquid 11 and the injection liquid 20 first discharged into the immersion fluid 11 through the first aperture 16 can be aspirated through the second aperture 17 with a second flow rate $Q_2$. The first and second flow rates $Q_1$, $Q_2$ may be generated using respective pumps (see FIG. 10).

Provided a specific ratio of $Q_2$ to $Q_1$ is maintained (e.g., 1.2-10, preferably 2-4), a laminar flow path C of processing liquid from the first 16 to the second 17 aperture can be obtained. Achieving such a laminar flow allows for hydrodynamic flow confinement. That is, the laminar flow C is hydrodynamically confined by the immersion liquid 11 within a confinement volume 21 that extends from below the first aperture 16 to below the second aperture 17. The size of the confinement volume 21 and the shape of the laminar flow C are notably controlled by the flow rates $Q_1$ and $Q_2$, the ratio of $Q_2$ to $Q_1$, $D_1$ and, in a less extent, $D_2$.

The flow rates $Q_1$ and $Q_2$, the ratio of $Q_2$ to $Q_1$ and the distance $D_2$ are extrinsic parameters, which depend on the actual operation method chosen. Assuming given dimensions for the apertures 16, 17, the only essential parameter that remains to be fixed is the distance $D_1$. In practice, the average diameter of the apertures may typically be between 0.5 and 1000 μm (at the level of the end surface 13). The ejection aperture 16 may, however, be designed small enough to enable a very local liquid confinement. Such a confinement (of e.g., 150 μm) is best obtained with a diameter of the ejection aperture 16 of about 20 to 50 μm. It can still be fabricated substantially smaller, e.g., 0.5 μm, which may be useful in some specific applications. The apertures 16, 17 end, each, a respective conduit (forming respective channels 14, 15) having preferably the same average diameter as their respective apertures. Yet, the sizes of the apertures 16, 17 may differ from each other (e.g., small outlet, large inlet). The aspiration aperture 17 may, in some cases, be much larger than the expected confinement size, especially where one seeks to prevent clogging by particles/dust. The dimensions retained for the apertures and their asymmetry strongly depends on the application sought. The flow characteristics enabled by the indicative dimensions given above are nevertheless suited for a wide range of applications. In particular, the distance $D_1$ between the apertures 16, 17 is preferably more than 5 μm, but also less than 2 mm. The diameter of the opening shall typically be small (typically one order of magnitude below, or more) compared to the distance $D_1$. With such dimensions, a stable confinement can in principle be achieved, while remaining practical from the fabrication standpoint.

Regarding the flow rates: for example, $Q_1$ may be chosen to be 1.0 fL/s-1.0 mL/s, and preferably 1.0-50 nL/s, while $Q_2$ may for example be chosen to be 1.2 fL/s-10 mL/s, preferably 2.0-200 nL/s.

FIG. 2 illustrates operation of the head 3 at a time where a target substance 22a has been carried away from the target area 2a by the laminar flow C and is being aspirated through the second aperture 17 into the second liquid channel 15. Based on timing considerations, or positioning data transmitted by the positioning system, the modulation unit proceeded to modulate the insertion of spacers 24 downstream of (i.e., before) a liquid volume comprising the target substance 22a, so as to encode metadata. Such metadata may notably encode information as to an address of the sample 2, its position, or the address/position of the specific target area 2a, or, still, an address of the particular liquid volume (or sequence thereof) enclosing the target substance 22a (or a sequence of captured target substances 22a-c), etc.

After retrieving the target substance 22a from the target area 2a, the microfluidic probe head 3 is positioned above the target area 2b so as for the confinement volume 21 to enclose a target substance 22b on top of target area 2b. The target substance 22b can be similarly carried away from the target area 2b by the laminar flow C and then aspirated through the second aperture 17 into the second liquid channel 15, along with processing liquid. Again, modulated spacers can be inserted downstream a corresponding processing liquid volume, if necessary. In variant, a single spacer may be inserted there, to merely separate the liquid volume comprising substance 2a from a liquid volume comprising substance 2b. Subsequently, the microfluidic probe head 3 can be positioned above the target area 2c in order to retrieve a target substance 22c, and so on. I.e., the steps of positioning the probe head 3 above the target areas 2a-2c and retrieving target substances 22a-22c can be repeated as many times as required in order to retrieve a sequence of target substances.

The target substances 22a-22c may for instance comprise biochemical substances. In, particular, the target substances 22a-22c may comprise a cell of a living organism and/or (a part of) a deoxyribonucleic acid (DNA), proteins, or other biological or chemical substances.

The spacer channel 18 delivers the spacer fluid 23 to the spacer junction 19 where the spacer fluid 23 is discontinuously inserted into the second liquid channel 15, at a spacer insertion rate $R_s$, so as to form droplet-shaped spacers 24 in this case. Accordingly, the fluid aspirated along the second liquid channel 15 comprises liquid volumes that are separated by the (modulated) spacers 24. Where needed, the rate $R_s$ can be varied, so as to encode metadata.

The injection liquid 20 may comprise a polar liquid, in particular a water-based or water-soluble liquid. The spacer fluid 23 may comprise a fluid that is immiscible with the injection liquid 20 and the immersion liquid 11. In particular, the spacer fluid 23 can comprise a nonpolar liquid and/or nonpolar solvent, e.g. a fat, an oil, a lipid, hexane or toluene.

FIG. 3 shows a more comprehensive view of a probe head 3 such as depicted in FIGS. 1 and 2. Here, an inlet 26 fluidly connects the first liquid channel 14 provided inside the body 12 to the injection liquid supply 6 located outside of the body 12. An outlet 27 fluidly connects the second liquid channel 15 provided inside the body 12 to the analyzer 8, the latter outside the body 12. A spacer inlet 28 fluidly connects the spacer channel 18 provided inside the body 12 to the spacer supply 7 located outside of the body 12.

A detection unit 29 is arranged inside the body 12. The detection unit 29 enables detection within a detection volume 30 inside the second liquid channel 15. This, in turns, allows to measure properties, e.g. a surface tension, a refraction index, a pH, a heat conductivity, an electrical conductivity, a viscosity, an impedance, a temperature and/or an inductance, of fluid passing through the detection volume 30.

This way, separate liquid volumes can be sensed and identified locally, i.e., directly at the level of channel 15. Upon identifying separate liquid volumes 25, the detection unit 29 may generate a detection signal and transmits it to the spacer modulation (e.g., and insertion) unit 31, to help synchronizing the spacer insertion, if necessary. The spacer modulation unit 31 controls the insertion rate $R_s$, at which the spacers 24 are inserted into the second liquid channel 15.

Now, the insertion rate $R_s$ may be synchronized with a positioning rate P, at which the microfluidic probe head 3 is changed position above the target areas 2a-2c, to ensure a correct separation of the liquid volumes containing respective target substances 22a-22c. Thus, information provided by the detection unit is optional, albeit useful for synchronizing purposes.

The insertion rate $R_s$ may for instance be defined as a number of spacers 24 inserted during a given time interval T, and the positioning rate P as a number of target areas 2a-2c processed by the head 3 during the same time interval T. Then, a synchronization of the insertion rate $R_s$ with the positioning rate P can be simply achieved by setting $R_s$ equal to P. Still, the insertion rate can be refined thanks to inputs provided from the unit 29, as described earlier.

However, should particular information need to be encoded at some point in the aspirated fluid, the spacer modulation unit 31 may timely modulate the insertion rate $R_s$ at which the spacers 24 are inserted, to modulate the insertion frequency and thereby encode the desired information. This modulation may notably be triggered by positioning information transmitted by the positioning system 4 and/or information retrieved directly from the detection unit 29.

The sequence of target substances 22a-22c, once enclosed in respective liquid volumes 25, is delivered to the outlet 27 via the second liquid channel 15 and from the outlet 27 further to the analyzer 8. The analyzer 8 may notably be configured for analyzing the retrieved target substances 22a-22c in the separate liquid volumes 25 in terms of chemical and/or biological properties. To that aim, the analyzer may be equipped with suitable detection means, to make it possible to decode information previously encoded by way of spacer modulation and use the information accordingly decoded to complete the analysis. The same detection means can also be used for analyzing the liquid volumes collected at the analyzer. The detection means (e.g., detection unit 29) can be optical (e.g., fluorescence, turbidity, absorbance, and the like), or capacitance/impedance measurements, for example. Such detection units 29 will typically be commercially available units with perhaps some level of customization for the application.

As evoked earlier, not only do the spacers allow encoding of information (when suitably modulated) but, in addition, they allow separation of liquid volumes, so that cross-contamination of the target substances 22a-22c can be prevented.

FIGS. 4A-4H illustrate preferred operation steps of a microfluidic probe head 3 such as depicted in FIG. 2. For conciseness, the Petri dish 10 and the body 12 of the microfluidic probe head 3 are not shown in FIG. 4.

In FIG. 4A, injection liquid 20 is delivered via the first channel 14 and discharges through the first aperture 16 into immersion liquid 11, with a first flow rate $Q_1$. At the same time, an underpressure is applied to the second liquid channel 15 such that fluid can be aspirated through aperture 17 into the second channel 15, with a second flow rate $Q_2$.

The target areas 2a-2c are again arranged in an array with a fixed distance from each other. Target substances 22a-22c are attached to respective target area 2a-2c immersed in the immersion liquid 11.

A suitable flow rate ratio is applied (as discussed earlier), to enable a laminar flow C of processing liquid between the apertures 16, 17, the injection is confined by the surrounding immersion liquid 11 within the confinement volume 21.

The probe head 3 is first positioned above the target area 2a such that a respective target substance 22a can be captured by liquid flowing in the confinement volume 21.

Meanwhile, information (e.g., position information, or information as to target 2a or array 2, etc.) is sent from the positioning system to the spacer modulation unit. The latter, may accordingly modulate the rate $R_s$ in view of modulating the spacer insertion, if necessary after a temporization delay, for synchronization purposes.

In FIG. 4B, the target substance 22a is detached from the target area 2a by the laminar flow C and gets aspirated into channel 15, via the second aperture 17. In the meantime, the microfluidic probe head 3 moves towards the next target area 2b, while spacer fluid 23 is pushed from the spacer channel 18 into channel 15 (via the junction 19), according to a rate $R_s$ modulated from the spacer modulation unit.

In FIG. 4C, the target substance 22a has now penetrated into channel 15 and moves upwards along the channel 15, preceded by a frequency modulated sequence of spacers. The frequency-modulated sequence of spacers is not complete yet. Indeed, a constriction of spacer liquid 23 forms downstream of (i.e., above) the target substance 22a, which extends from the spacer channel 18. In the meantime, the microfluidic probe head 3 is positioned above target area 2b, whereby a respective target substance 22b gets captured inside the confinement volume 21.

In FIG. 4D, the constriction is now cut off from the remaining part of the spacer fluid 23 and forms a well-defined droplet-shaped spacer 24a, terminating the modulated spacer sequence moving upwards at flow rate $Q_2$. The sequence latter may for instance be used to encode information as to the targets 2a-c. The last spacer 24a of the sequence precedes a liquid volume that contains substance 22a. Meanwhile, target substance 22b has been detached from target area 2b and is carried towards aperture 17, while the head 3 is moved towards the target area 2c.

The process is repeated as shown throughout FIGS. 4E-4H, except that, from this moment on, a single spacer is inserted between each liquid volume of interest. To that aim, spacer fluid 23 is synchronously inserted into the second liquid channel 15. This way, a sequence of separate liquid volumes can be formed, with liquid volumes separated from one another by spacers, and which contains a respective target substance. As described above, metadata was encoded downstream (i.e., on top) of this sequence, for later analysis. If necessary, additional metadata may be encoded upstream, to close the sequence. The spacers modulated downstream and upstream of this sequence may be regarded as header and footer, respectively. This will be discussed later in more detail.

Figure 5:
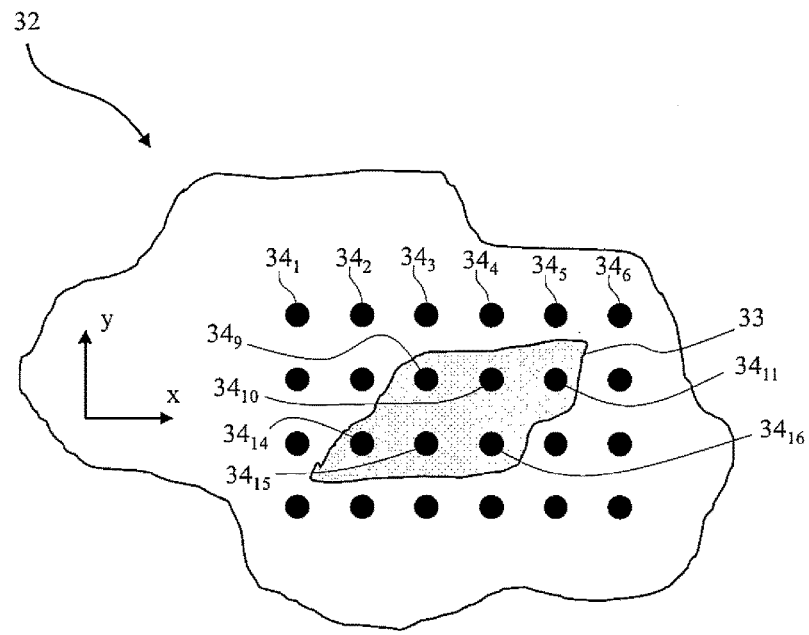
FIG. 5 shows a schematic view of a part of a tissue section comprising tumorous cells.

FIG. 5 shows a schematic view of a tissue section 32 containing a tumorous area 33. An array of target areas $34_1$-$34_{24}$ is arranged on a surface of the tissue section 32. A probe head 3 as described herein may be used to retrieve samples from each of the target areas $34_1$-$34_{24}$ and delivers them to the analyzer 8 (FIG. 1). For example, the analyzer 8 may be configured for determining a ratio $R_T$ of tumorous cells to healthy cells of each of the samples and allocating the ratio to the respective target area $34_1$-$34_{24}$. This facilitates a spatial mapping and a localization of the tumorous cells in the tissue section 32. In this example, the samples from the target areas $34_9$-$34_{11}$, $34_{14}$-$34_{16}$ will show a high $R_T$, whereas the samples from outside of the tumorous area 33 result in a low $R_T$. This way, a cancer heterogeneity (in terms of the spatial distribution) and/or a progression front of a tumor can be investigated.

Applications of the present probes are, however, not limited to cancer/tumor research, but extend to any analyte. For example, present probes may be used to perform a precise localization of DNA and single cells in a microarray, i.e. a system of regularly arranged samples, analytes, and/or other (bio)chemical substances.

Figure 6:
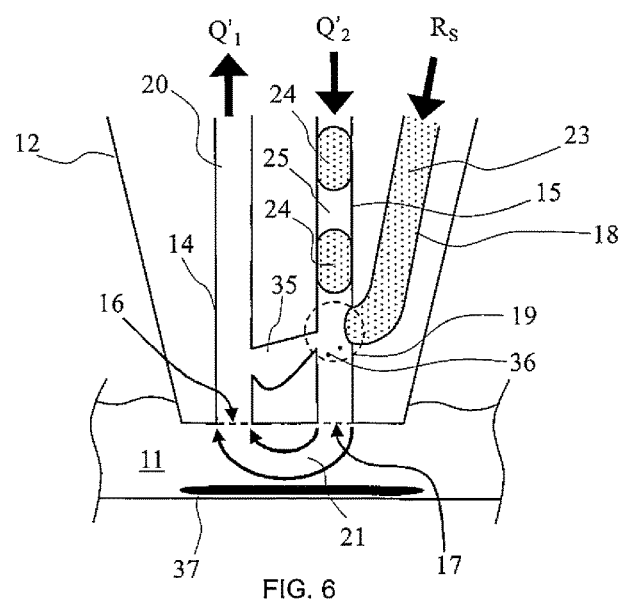
FIG. 6 is a cross-sectional view of a simplified representation of a variant to the microfluidic probe head of FIG. 2.

FIG. 6 shows a cross-sectional view of a simplified representation of a variant to the microfluidic probe head of FIG. 2. Here the probe head 3 is similar to that of FIG. 2, except that the head 3 now comprises a fluid bypass 35 that fluidly connects the first and second channels 14, 15 to each other. In addition, blocking elements 36 (i.e., capillary structures such as posts) are provided for redirecting spacers 24 into the fluid bypass 35.

Furthermore, and in comparison to the embodiment of FIG. 2, the first and second flow rates $Q_1$, $Q_2$ can be changed, to reverse an operation mode of the head 3. Namely, the probe head 3 has a reversed operation mode for depositing a sequence of processing liquid volumes 25 (possibly including substances to be deposited) in addition to a normal operation mode where it retrieves target substances, as described earlier in reference to FIG. 2. In the reversed operation mode, the flow directions are reversed, such that liquid in the first channel 14 flows towards the inlet 26 (FIG. 3), while liquid in the second channel 15 flows towards the second aperture 17.

A sequence of separate liquid volumes 25 (separated by spacers 24) can be delivered to the second aperture 17 with flow rate $Q'_2$. At the first aperture 16, processing liquid volumes and part of the immersion liquid 11 are aspirated into channel 14 with a flow rate $Q'_1$. The rate $Q'_1$ is now greater than $Q'_2$, and a ratio of $Q'_1$ to $Q'_2$ may be chosen along the same values as discussed earlier (e.g., 1.2-10), with $Q'_1$ being e.g., 0.2 fL/s-4.0 mL/s, and $Q'_2$ being e.g., 1.0 fL/s-1.0 mL/s, to form a reversed laminar flow C' and hydrodynamic flow confinement thereof.

By positioning the microfluidic probe head 3 above deposition area 37, part of the liquid of the reversed flow C' will contact the deposition area 37. By repeating the steps of positioning the head 3 and feeding the sequence of liquid volumes 25 through the confinement volume 21', separate processing liquid volumes 25 may come to process respective deposition areas.

The blocking elements 36 redirect the spacers 24 into the fluid bypass 35 and thereby prevent the spacers 24 from reaching the second aperture 17 and discharging into the immersion liquid 11. In turn, this prevents the spacers 24 to come into contact with the deposition area 37, a thing that may alter the properties of and contaminate the deposition area 37, in particular if spacers comprise an oil-phase.

Referring now to FIG. 8, embodiments of the present microfluidic probes may further comprise a spacer removal module, including e.g., a channel 38 fluidly connected to the first channel 14, via a spacer removal junction 39. Such a spacer removal module 38 is configured for removing liquid spacers 24 from the first channel 14, via the spacer removal junction 39. To that aim, blocking elements 40 (i.e., capillary structures such as posts) may be provided in the first channel 14 at the level of the spacer removal junction 39. The blocking elements 40 operate similarly as their counterpart elements 36 of FIG. 6. Owing to the nature of processing liquid (e.g., aqueous) and liquid spacers (e.g., oil) typically used, the capillary structures 40 will typically provide low resistance to the processing liquid and a high resistance to the spacers, urging the latter into the spacer removal channel 38. Note that blocking elements 40 may be provided in the second channel 15 too, in a symmetrical fashion, to allow reverse operation of the probe head 3 and liquid re-circulation.

In that respect, the present probes may further comprise suitable pressure sources, configured to apply pressures to the first and second channels 14, 15, as well as pressure control means $Q_1$ and $Q_2$ operatively coupled to these pressure sources, so as to controllably switch a flow direction of liquid in each of the channels 14, 15. This way, reverse operation of the probe head 3 and liquid re-circulation can be achieved. It is noted that the pressure control means $Q_1$, $Q_2$ may be pressure control units, such as standard off-the-shelf pressure/flow control units. These can be produced by and sourced from many vendors, for example Fluigent, Cetoni, Elveflow, and the like.

Figure 9:
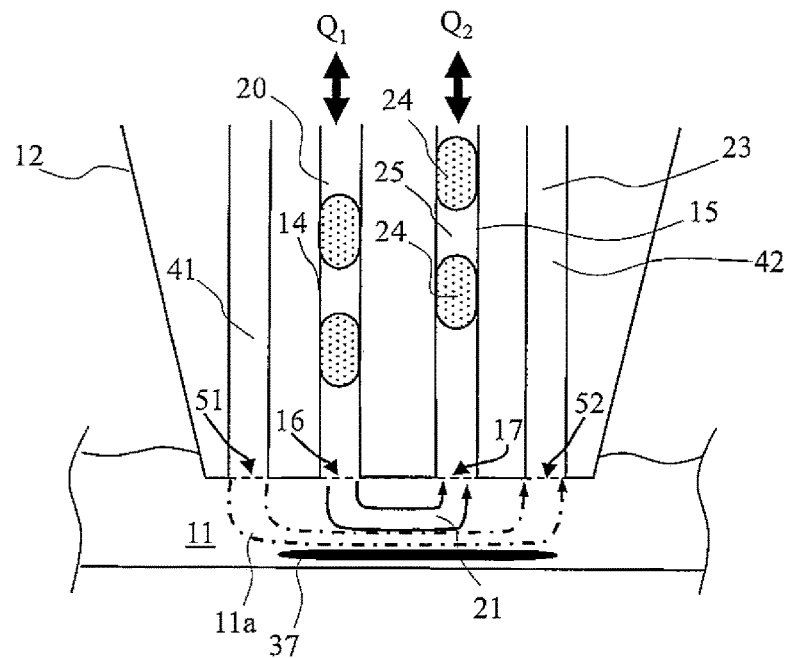
FIG. 9 shows a variant to the probe head of FIG. 2, allowing processing liquid to be shaped by a shaping liquid enabled by additional channels and apertures, as involved in embodiments.
Figure 10:
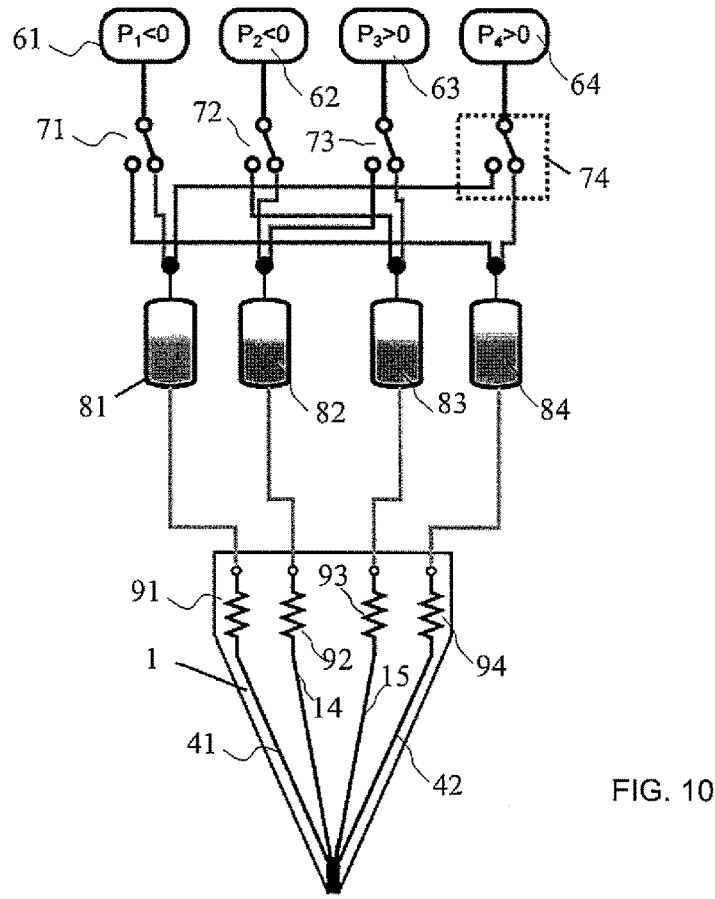
FIG. 10 shows a more comprehensive view of a probe head as in FIG. 9, notably illustrating pressure sources and respective valves to switch flow directions in the channels, as involved in embodiments.

Referring now to FIGS. 9 and 10 altogether, the present probes may further comprise, in embodiments, a third channel 41 and a fourth channel 42. Channels 41, 42 are in fluid communication with a third aperture 51 and a fourth aperture 52, respectively, where each of the apertures 51, 52 is provided on said face 13, e.g., on each side of and along the same direction subtended by apertures 16, 17. This way, a flow path going from aperture 16 to aperture 17 may be shaped by, e.g., confined within, shaping liquid 11a provided through the third aperture 51.

The apertures 51, 52 may be adequately dimensioned and located on the end face 13 so as to enable a laminar flow of shaping liquid 11a and, in particular, to make it possible to re-aspirate shaping liquid at the fourth aperture 52. They are typically larger than the apertures 16, 17, to make it possible to confine a flow path 21 enabled by the latter. Here, a double flow confinement is contemplated: the flow path 21 is confined within the flow of the liquid 11a, which itself is confined within the immersion liquid 11.

As illustrated in FIG. 10, one or more of (and preferably all) the channels 14, 15, 41, 42 may, each, comprise a hydrodynamic flow resistor 91-94. The flow resistors 91-94 are located between respective reservoirs 81-84 (subject to switchable pressure sources 61-64) and apertures 16, 17, 51, 52. In the inner channels 14, 15, the hydrodynamic flow resistors are preferably located between respective reservoirs and spacer insertion junctions (e.g., junction 19 for channel 15, see FIG. 8). The hydrodynamic flow resistors make it possible to curb liquid bursts caused upon switching flow directions, e.g., where reverse operation or liquid re-circulation is contemplated.

In particular, pressure sources 61-64 may be provided to apply a pressure in each channel 14, 15, 41 and 42, together with pressure control means 71-74, 81-84. The pressure control units 61-64 may be standard off-the-shelf pressure/flow control units. These can be produced by and sourced from many vendors, for example Fluigent, Cetoni, Elveflow, and the like. The pressure control means 71-74, 81-84 are operatively coupled to the sources 61-64 to controllably switch a flow direction of liquid in each channel pair. That is, liquid flow direction can accordingly be switched, on the one hand, in each of the first and second channels 14, 15, and, on the other hand, in each of the third and fourth channels 41, 42. The pressure control means 71-74 may be switch, valves that are commercially available off-the-shelf components. They are here used for switching the pressure. Preferably, four pressure sources 61-64 are used, which respectively connects to four valves 71-74 to switch flow directions in each pair of channels. The valves may for instance selectably connect, each, a given pressure source to one of two reservoirs 81-84 that fluidly connect to a respectively channel. As seen in FIG. 10, four reservoirs 81-84 may be provided, which fluidly connect, each, to a respective channel 41, 14, 15, 42, via a respective hydrodynamic flow resistor 91-94. The valves can switch the pressure polarity so as to reverse flow directions in each pair of channels. This makes the device fully amenable to fluid recirculation in each pair of channels.

According to another aspect, the invention can be embodied as methods for modulating liquid spacers 24 separating liquid volumes 25 in a microfluidic probe 1 such as described above. Steps involved in such methods have already been essentially described above in reference to FIGS. 2-8.

Briefly, and according to such methods, liquid spacers 24 are inserted into a processing liquid channel 15, via a spacer insertion junction 19, to obtain a sequence of liquid volumes 25 separated by the spacers 24. Spacers are inserted while moving processing liquid in the processing liquid channel, as for instance discussed in reference to FIGS. 2-8. In addition, the insertion of liquid spacers 24 can be modulated, e.g., so as to encode information. The modulation may notably concern the spacer insertion rate (or frequency), although other types of modulation are possible, as discussed earlier. Encoding is typically done via the spacer modulation unit 31. The encoded information may then subsequently be decoded, e.g., remotely, during a subsequent analysis.

Figure 4:
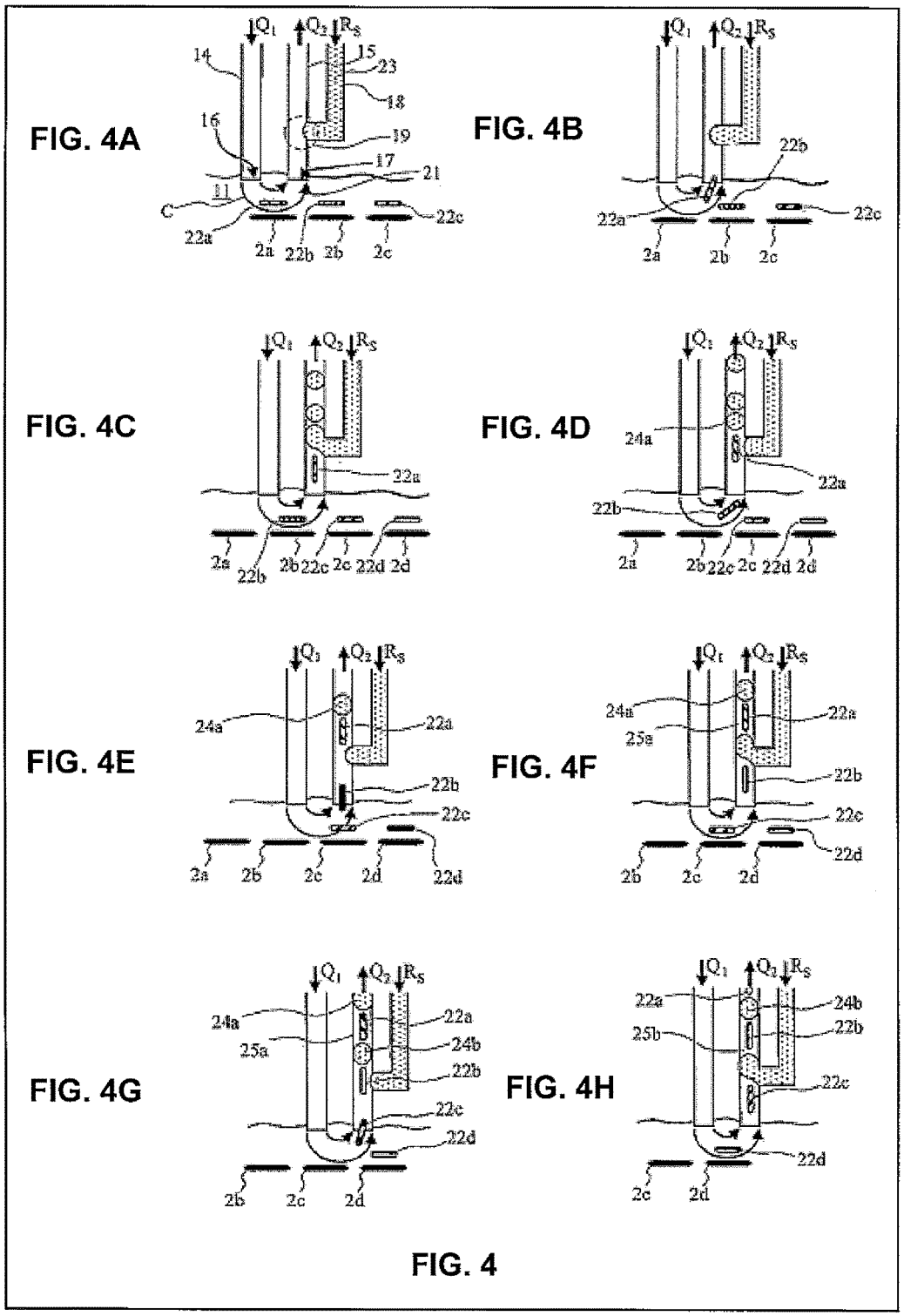
FIG. 4, which includes

As already discussed in reference to FIGS. 1 and 4, the probe head 3 may be positioned with its end face 13 at given positions vis-à-vis a surface to be processed. Then, the modulation unit 31 may proceed to timely modulate the insertion of spacers 24 according to position data for said given positions, e.g., as transmitted from the positioning means 4, or based on timing consideration, as explained earlier.

Present methods make it further possible to encode metadata in the form of headers and/or footers, as described now in reference to FIGS. 1, 11. Namely, in embodiments, the probe head 3 may be positioned at a first position, i.e., with the end face 13 vis-à-vis a surface to be processed. Then, the insertion of spacers 24 in the processing liquid channel can be modulated to encode a header and/or a footer. The header and/or the footer are respectively encoded downstream and/or upstream (i.e., before and/or after) a given liquid volume, i.e., a liquid volume (or a sequence of volumes separated by spacers) that has been used to process the surface at said first position. Consistently, the encoded header and/or footer are, each, interpretable as metadata pertaining to said given liquid volume (or sequence of volumes) or, equivalently, a target area or surface portion that has been processed by said liquid volume (or sequence), etc. This makes it possible to identify a given liquid volume (or sequence) and/or associate it to a corresponding sample, array, etc., or a location thereof.

After having completed the processing of the first target area, the above steps of positioning, processing and modulating can be repeated at a second position, and so on.

Preferably, modulating the insertion of spacers is performed so as to encode both a header and a footer. Between the header and the footer, the sample flow can be segmented using single spacers, as described earlier. However, only a header or a footer may be used. Headers and footers are preferably inserted while the probe approaches or retracts from the surface, as illustrated in FIG. 11A-B, for efficiency. Beside headers and footers, any useful spatiotemporal information about the sample(s) may be encoded into the flow, as a 'signature' that can be later decoded, e.g., during downstream processing.

Decoding and interpreting the encoded data may be performed remotely, as discussed now in reference to FIG. 12. In embodiments, present methods may further comprise decoding information previously encoded by spacer insertion modulation. This operation is typically performed remotely, e.g., at an analyzer, and is preferably achieved by measuring changes in a capacitance (as assumed in FIG. 12) of the processing liquid moved in the processing liquid channel, or by fluorescence, using known characterization techniques.

In FIG. 12A, a sensor signal is acquired, from which a spacer frequency can be deduced (e.g., using fast Fourier transform, FIG. 12B). With reference to FIG. 12C, the varying frequencies are next interpreted in terms of information, e.g., first a location (e.g., x, y, z coordinates) of a processed sample, and then a 'start' signal, indicating the beginning of a liquid volume (or sequence of volumes) (e.g., "Data arriving"). The last frequency may correspond to mere liquid volumes separated by single spacers, as described in reference to FIG. 4 (FIG. 12 is not to scale).

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

The invention claimed is:

1. A microfluidic probe comprising:
a probe head comprising: a processing liquid channel in fluid communication with a processing liquid aperture on a face of the probe head, the probe head configured to move processing liquid in the processing liquid channel toward and/or from the processing liquid aperture;
a spacer supply unit fluidly connected, via a spacer insertion junction, to the processing liquid channel, the spacer supply unit configured for inserting liquid spacers into the processing liquid channel, via the spacer insertion junction, to obtain liquid volumes separated by inserted liquid spacers; and
a spacer modulation unit configured to:
modulate an insertion of spacers via selectively controlling the spacer supply unit; and
encode retrievable information pertaining to the liquid volumes between the inserted spacers by modulating the insertion of the spacers according to specific information to be encoded.

2. The microfluidic probe according to claim 1, wherein the spacer modulation unit modulates one or more of:
a frequency of insertion of spacers;
a length of inserted spacers; and
a number of spacers successively inserted.

3. The microfluidic probe according to claim 1, further comprising:
a positioning system for positioning the microfluidic probe head at given positions; and transmitting position data for said given positions,
wherein the spacer modulation unit is further connected to the positioning system so as to modulate an insertion of spacers according to position data transmitted by the positioning system.

4. The microfluidic probe according to claim 1, the probe head further comprising:
a first aperture channel in fluid communication with a first aperture on said face, the first aperture and the second aperture at a distance of each other, said distance designed so as to make it possible for the probe to aspirate at the second aperture processing liquid delivered through the first aperture.

5. The microfluidic probe according to claim 4, further comprising:
a spacer removal module fluidly connected to the first channel, via a spacer removal junction; and
blocking elements arranged in the first channel at a level of the spacer removal junction, wherein the spacer removal module and the blocking elements are configured for removing liquid spacers from the first channel, via the spacer removal junction.

6. The microfluidic probe according to claim 5, further comprising:
pressure sources configured to apply pressures to the first channel and the second channel; and
pressure control means operatively coupled to the pressure sources to controllably switch a flow direction of liquid in each of the first channel and the second channel.

7. The microfluidic probe according to claim 6, wherein the second channel comprises a hydrodynamic flow resistor between a respective one of the pressure sources and the spacer insertion junction, the hydrodynamic flow resistor adapted to curb a liquid burst caused upon switching said flow direction via the pressure control means.

8. The microfluidic probe according to claim 4, further comprising:
a third aperture channel and a fourth aperture channel, in fluid communication with a third aperture on said face and a fourth aperture on said face, respectively, wherein the probe head is configured to allow processing liquid in a flow path going from the first aperture to the second aperture to be shaped by shaping liquid provided through the third aperture.

9. The microfluidic probe according to claim 8, further comprising:
pressure sources configured to apply a pressure in each of the first aperture channel, the processing unit channel, the third aperture channel and the fourth aperture channel; and
pressure control means operatively coupled to the pressure sources to controllably switch a flow direction of liquid, on the one hand, in each of the first aperture channel and the processing unit channel, and, on the other hand, in each of the third aperture channel and the fourth aperture channel.

10. A method comprising:
while moving processing liquid in a processing liquid channel toward and/or from a processing liquid aperture, inserting liquid spacers into the processing liquid channel, via a spacer insertion junction at the processing liquid channel, to obtain a sequence of liquid volumes separated by the spacers, wherein the liquid spacers separating liquid volumes are in a microfluidic probe, the probe comprising a probe head, the probe head having the processing liquid channel in fluid communication with the processing liquid aperture on a face of the probe head, and
modulating the insertion of the spacers selectively to encode retrievable information pertaining to the liquid volumes between the inserted spacers according to specific information to be encoded.

11. The method according to claim 10, wherein modulating comprises:
modulating one or more of: a frequency of insertion of spacers inserted at inserting the liquid spacers; a length of the spacers inserted at inserting the liquid spacers; and a number of spacers successively inserted at inserting the liquid spacers.

12. The method according to claim 10, further comprising:
decoding information previously encoded by measuring changes in a capacitance of processing liquid comprising modulated spacers inserted therein.

13. The method according to claim 10, further comprising:
positioning the microfluidic probe head with said face vis-à-vis a surface to be processed via the probe head, at given positions with respect to the surface; and
accessing position data for said given positions, wherein modulating the insertion of spacers is performed according to the accessed positions.

14. The method according to claim 13, further comprising:
   positioning the microfluidic probe head at a first one of the given positions;
      while processing the surface with the probe head at said first one of the given positions, whereby processed liquid is aspirated in the processing liquid channel via said processing liquid aperture, modulating an insertion of spacers in the processing liquid channel to encode a header or a footer, respectively downstream or upstream a given liquid volume of processed liquid moving in the processing liquid channel from the processing liquid aperture, the encoded header or footer interpretable as metadata pertaining to said given liquid volume; and
      after having completed processing of the surface at the first one of the given positions, repeating the steps of positioning, processing and modulating, at a second one of the given positions.

15. The method according to claim 10,
wherein said processing liquid channel is a second channel and said processing liquid aperture is a second aperture,
wherein the probe head further comprises: a first channel in fluid communication with a first aperture on said face, and
wherein the method further comprises: aspirating at the second aperture processing liquid delivered through the first aperture.

16. The method according to claim 15, further comprising:
   removing liquid spacers from the first channel, via a spacer removal junction at the first channel.

17. The method according to claim 16, further comprising:
   applying pressures to the first channel and the second channel to trigger a flow of processing liquid from the first channel to the second channel; and
   changing the applied pressures to switch a flow direction of the flow of processing liquid.

18. The method according to claim 15, wherein the probe head further comprises:
   a third channel and a fourth channel, in fluid communication with a third aperture on said face and a fourth aperture on said face, respectively, wherein the method further comprises:
   shaping processing liquid provided through the first aperture with shaping liquid provided through the third aperture.

* * * * *